United States Patent [19]

Hale

[11] 4,074,887
[45] Feb. 21, 1978

[54] POWER UNIT FOR A MEDICAL OR LIKE STOOL

[76] Inventor: Dean H. Hale, 2424 N. Main St., Logan, Utah 84321

[21] Appl. No.: 724,889

[22] Filed: Sept. 20, 1976

[51] Int. Cl.² .................................. F16M 11/00
[52] U.S. Cl. ............................. 248/404; 248/400
[58] Field of Search ............ 248/161, 162, 404, 400; 297/345, 347

[56] References Cited

U.S. PATENT DOCUMENTS

| | | | |
|---|---|---|---|
| 633,021 | 9/1899 | Mason | 248/413 X |
| 2,947,556 | 8/1960 | Wenger | 248/161 X |
| 3,147,946 | 9/1964 | Hale | 248/404 |
| 3,381,926 | 5/1968 | Fritz et al. | 248/404 |
| 3,865,341 | 2/1975 | Fortnam et al. | 248/404 |
| 3,921,952 | 11/1975 | Wirges | 248/404 |

FOREIGN PATENT DOCUMENTS

| | | | |
|---|---|---|---|
| 1,197,187 | 7/1970 | United Kingdom | 297/345 |

*Primary Examiner*—Lawrence J. Staab
*Attorney, Agent, or Firm*—Lynn G. Foster

[57] ABSTRACT

A novel mechanical power unit for use in stool and the like construction having features allowing its easy application to great variety of additional uses. The power unit has a ram which is displaced within a cylinder under the influence of hydraulic fluid driven by compressed air. The fluid and compressed air are carried in a reservoir generally surrounding the cylinder, formed by the outer wall of the cylinder and the inner wall of a generally concentric shell welded permanently at its ends to the cylinder. A manually operable, normally closed valve is provided in the base of the cylinder to control transfer of fluid between the interior of the cylinder and the reservoir to operate the power unit, causing the ram to extend or retract with respect to the cylinder, and holding the ram in any amount of extension when the valve is closed. The ram end of the reservoir shell is shaped to form a pressure retaining dome, and the ram carries an adapter for ready attachment to any object to be powered, such as the seat of a stool. The opposing end of the reservoir shell is tapered to provide removable frictional engagement with a base, such as the floor-engaging part of the stool.

4 Claims, 3 Drawing Figures

POWER UNIT FOR A MEDICAL OR LIKE STOOL

BACKGROUND

1. Field of Invention

The present invention relates broadly to a power unit and more particularly to a novel power unit which can be readily used for medical and like stools, the length of which can be extended and retracted at will by the operator, and which comprises a ram, and cylinder in which the ram slides, an integral reservoir of oil pressurized by air, a valve or flow control, and at least one seal.

2. Prior Art

Ram power units for extending and retracting a ram within a cylinder have traditionally used oil or hydraulic reservoirs generally adapted only to the particular use to which the power unit is employed. Often the reservoir has been built into structures which actually form a part of an assembly including a ram power unit, so that use of the power unit in other applications has required additional adaptations and designs of the reservoir to be consistent with these other applications. While oil reservoirs have on occasion been built into the structure of the power unit itself, the reservoir has been made up of a multiplicity of component parts, including tubes, plugs, seals and fastening means, to make-up the reservoir. Further, such units have not been readily interchangeable or adapted to uses for other purposes.

BRIEF SUMMARY AND OBJECTS OF THE INVENTION

With the foregoing in mind, the present invention provides a novel and versatile power unit comprising a ram displaceable within a cylinder within which the ram moves, and a novel fluid and air reservoir. Maximum adaptability of the unit to the powering of various objects is provided, with minimum adaptative alterations being required for either the unit or the objects powered. Maximum power stroke length is provided within a compact envelope, and the unit is of reduced weight, while being capable of high fluid operating pressures and high load capacities. The unit is manually operable and the length extent and location of the power strokes are selectable for optimum adaptability to various uses.

With the foregoing in mind it is a primary object of this invention to provide a novel power unit for relatively displacing a ram and cylinder.

It is another primary object of the invention to provide a novel fluid and air reservoir for a power unit having a ram and a cylinder.

It is a further object of the invention to provide an outer shell, forming with a cylinder in which a ram moves, a fluid and air reservoir, the shell being permanently attached to the cylinder.

It is a further object to provide a compact power unit package having a maximum length power stroke.

It is an object of the invention to provide a reduced weight power unit capable of high operating pressures and high loads thereon.

It is an object of the invention to provide a power unit having a ram which may be extended and retracted at the will of the operator.

It is a further object of the invention to provide a power unit having a ram which may be rapidly extended and may be smoothly retracted at a controlled rate.

It is a further object of this invention to provide a self contained power unit having maximum adaptability to various applications.

These and other objects and features of the present invention will become more fully apparent from the following description and appended claims taken in conjunction with the accompanying drawings.

DETAILED DESCRIPTION OF THE ILLUSTRATED EMBODIMENT

Figure 1:
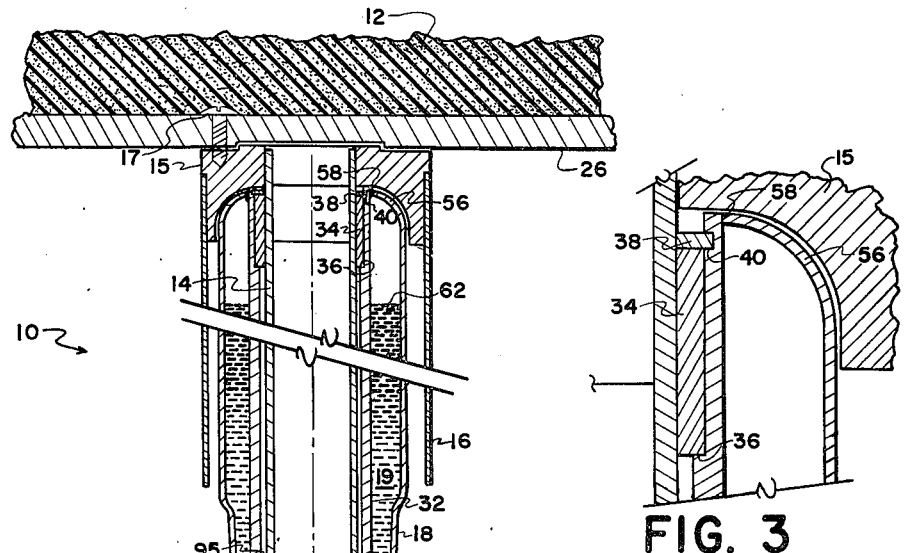
FIG. 1 is a cross sectional representation taken longitudinally through the center of a presently preferred power unit according to the present invention, which is shown adapted to an adjustable stool.

Referring now to the Figures, the power unit, generally designated 10, is illustrated as forming part of a vertically displaceable stool, although the power unit can and may be used in any of a wide variety of compatible structures and may be disposed in any desired orientation. Referring to FIG. 1 in particular, the power unit 10 is illustrated as carrying a seat 12. The unit 10 carries a connecting adapter 15 used in this illustrated application to mount the seat 12, which is attached thereto by means of mounting screws 17 through the seat mounting plate 26. The adapter 15 has a permanently attached depending skirt 16 which telescopes over and is movable vertically relative to the unit 10. The unit 10 is positioned in a socket 20 of a base 22, the base carrying casters 31.

The depending skirt 16 protects moving parts of the power unit 10 from dust and other foreign particles. A valve actuating lever 28 is mounted on the base 22 and is manually movable or pivotal toward the underside of the power unit 10 to permit elevating or lowering of the seat as hereinafter more fully described.

Figure 2:
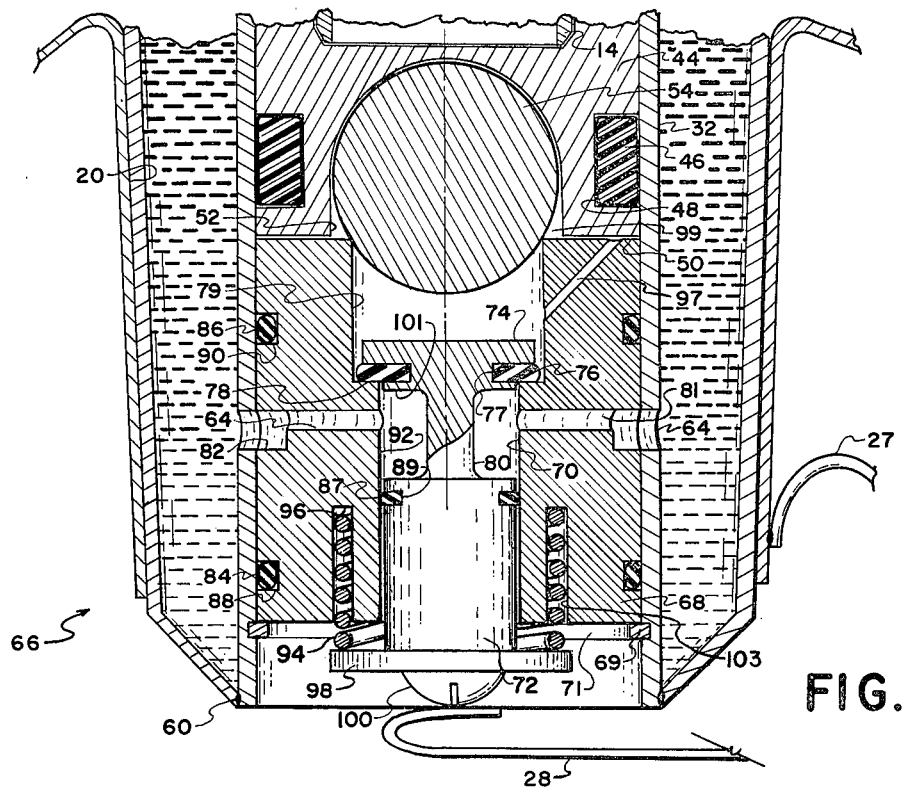
FIG. 2 is an enlarged scale cross sectional detail of the lower end of the power unit, showing the manual flow control valve and associated details.

The power unit 10 comprises a tubular ram 14 shown in FIGS. 1 and 2 in its lowermost position, movable within a tube 32 under the influence of fluid pressure on a face 50 on the lower end of the ram 14, pressurized fluid being contained in a reservoir 19 defined between a shell 18 and the outermost surface of the tube 32 and being communicated to the surface 50 through a valve structure generally designated 66 manually controlled by the actuating lever 28. The valve 66 is opened both to extend, and to retract, the ram 14, as hereinafter more fully described. A check valve ball 54 generally permits gradual smooth lowering, but rapid raising, of the seat 12, also more fully described hereinafter.

Figure 3:
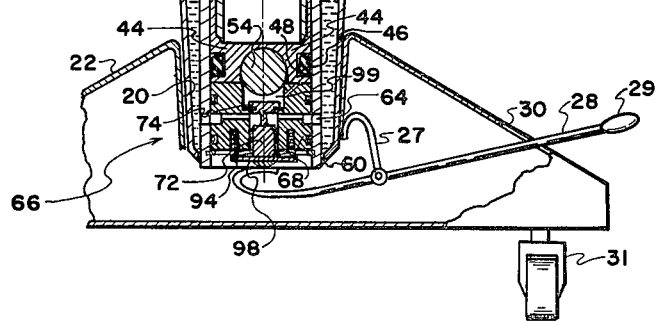
FIG. 3 is an enlarged scale cross sectional detail of a portion of the upper extremity of the reservoir.

The post 14 telescopes slideably into the cylindrical tube 32 and is guided by a sleeve 34 in the top of the tube 32, resting on a shoulder 36 in the tube 32 and held in place by a snap ring 38 held by a groove 40 in the tube 32. (See FIG. 3) The bottom end of the post 14 is closed by a plug 44, the plug 44 being attached by a weld 95 to the post 14 and carrying a seal 46 in a circumferential groove 48 to prevent passage of air or hydraulic fluid thereby. In a manner hereinafter described, fluid pressure is applied to the face 50 of the plug 44 to raise the post 14 carrying the seat 12. The plug 44 has a recess 52 to accept a check valve ball 54 when the post 14 is in its lowermost position, the function of which ball is hereinafter described.

The structure by which fluid pressure is applied to the lower face 50 of the plug 44 closing the post 14 will now be described. The cylinder 18 is curved inward at its upper extension forming a pressure retaining partial dome 56 secured circumferentially to the outside surface of cylinder 32 by a continuous weld 58. (See FIG. 3) The lower extension of the cylinder 18 is shaped in a similar fashion and secured by a corresponding circumferential weld 60 to the lowermost extension of the tube 32. (See FIG. 2) The shell 18 and the post 32 define a reservoir 19 therebetween for pressurized gas and fluid. This reservoir 19 is filled with hydraulic fluid to a level 62, above which the reservoir is filled with compressed air. Near its lower end, tube 32 has a series of circumferentially spaced orifices 64, communicating with a valve structure generally designated 66, which may be selectively opened or closed to permit or prevent communication of fluid between the reservoir 19 and the interior of tube 32.

The valve structure 66 comprises a valve body 68 containing a central bore 70 carrying a valve stem 72. (See FIG. 2) The valve body 68 is retained in the cylinder 32 by a snap ring 69 installed in a groove 71 carried by the interior wall of cylinder 32. (See FIG. 2) The valve stem 72 carries a valve head 74 which carries a seal 76 in a circumferential groove 77. The seal 76 contacts a seat 78 formed by an enlargement 79 of the bore 70. The valve stem 72 has also a section of reduced diameter 80, located immediately below a close tolerance flange 101, reciprocally disposed within the bore 70. A plurality of radial passages 81 are provided in the valve body 68 extending radially from the bore 70 to a circumferential groove 82 in the valve body 68. This circumferential groove 82 communicates with the radial orifices 64 through the tube 32 hereinbefore described so that fluid from the reservoir 19 may flow therethrough.

The body 68 carries seals 84 and 86 in circumferential grooves 88 and 90, respectively, of the valve body 68, these seals preventing the passage of fluid between the outer surface of the body 68 and the inner wall of the tube 32. The stem 72 carries a seal 87 in a circumferential groove 89 to prevent leakage of fluid downwardly around the stem 72. The central bore 70 extends to the bottom of the body 68 an insure that the stem 72 does not appreciably wobble during displacement. The stem is biased to its closed, sealed position illustrated best in FIG. 2 by a spring 94, which acts between the base surface 96 of an annular groove 103 formed in the bottom of body 68 and a washer 98 held on the bottom of stem 72 by a screw 100. Thus, the spring 94 biases the seal 76 into closing contact with the seat 78. The spring 94 may be compressed by manual actuation of the lever 28, opening the valve structure 66 so fluid may flow between the reservoir and the interior of the tube 32.

The check valve ball 54 movably contacts the seat 99 formed by the upper circumferences of the bore 79 to restrict flow of fluid downwardly out of the interior of the tube 32 when the valve stem 72 is raised and fluid inside the tube 32 may be pressurized as hereinafter described, urging the fluid to flow downwardly through the valve structure into the reservoir 19. However, one or more restricted flow passages 97 are provided through the valve body 68, so that fluid flows downwardly at a reduced rate under these conditions.

When the post 14 is in its lowermost position as shown in FIGS. 1 and 2 the fluid is substantially all contained in the reservoir 19 comprised of the walls of the cylinder 32 and shell 18, so that the compressed gas in the reservoir occupies its most reduced volume above the level 62. When it is desired to raise the post and the stool seat 12, the lever 28 is manually actuated downward, thereby raising stem 72 and allowing fluid to pass from the reservoir through the valve structure 66 to apply pressure to the bottom face 50 of the plug 60 closing the end of the post 14. As the post rises under the influence of fluid pressure, check valve ball 54 is displaced from the seat 99, allowing rapid flow into the interior of the post 32, raising the post 14 rapidly until the lever 28 is released, at which time the valve stem 72 returns to its sealing position under the influence of the spring 94. The post 14 and the seat 12 remain in their now raised position so long as the valve structure 66 is allowed to remain closed. In its uppermost position the post 14 is stopped when a shoulder formed by the weld 95 on the plug 44 contacts the lower end of the sleeve 34, located at the upper end of cylinder 32, (See FIGS. 1 and 3).

When the occupant of the seat 12 desires to lower the elevated seat 12, he opens the valve structure 66 manually by actuating the lever 28 while allowing his weight to rest upon the seat 12, which weight forces the post 14 downward to force fluid in a reverse direction through the valve 66 held open by the position of the lever 28. As soon as this reverse flow of fluid starts, however, the valve check wall 54 is urged by the reverse fluid pressure against the seat 99 on the valve body 68. The reverse flow is thus blocked except as permitted by the orifices 97 which bypass the seat 99. This restricted reverse flow limits the rate of descent of the seat structure resulting from the weight applied to post 14. Thus the seat 12 and the occupant are always assured of a gentle descent until the valve structure is closed by release of the lever 28, halting the reverse flow of fluid entirely. The occupant is also thus assured of a gentle bottoming should the seat 12 and the post 14 be allowed to descend to their lowermost position as shown in the Figure.

The portion of the reservoir above line 62 is preferably filled with compressed air and the portion of the reservoir below the dashed line 62 and the interior of the tube 32 preferably contains hydraulic fluid. An air inlet valve, not shown, is provided in the lower portion of the cylinder 18 so that compressed air may be introduced periodically for recharging the reservoir 19 with air.

The lever 28 has a pedal 29 and is pivotally attached to a rigid fulcrum arm 27 which in the illustrated embodiment 10 is attached by weld 23 to the interior of base 22. (See FIGS. 1 and 2) The lever 28 acts through an aperture 30 in the base 22 which provides sufficient clearance for the lever to be actuated by the foot of the stool occupant.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What is claimed and desired to be secured by United States Letters Patent is:

1. A power unit for advancing and retracting an object comprising:

hollow cylindrical ram means comprising means at one end of the hollow ram means adapted to be connected to said object and closure means entirely closing the other end of the ram means, said ram means being relatively reciprocable between extended and retracted positions;

elongated hollow reservoir forming means co-axially and, when in the retracted position, substantially co-extensive with the ram means, the reservoir means comprising a generally elongated annular reservoir cavity defined by a cylindrical inner wall juxtaposed and relatively reciprocable in respect to the ram means, and a generally cylindrical U-shaped outer wall spaced from said inner wall, the respective ends of the inner and outer walls being integrally connected to each other, said inner wall comprising port means adjacent one end thereof, the outer wall conically converging at one end thereof, the reservoir cavity containing liquid and pressurized gas acting upon and selectively displacing the liquid through the port means;

valve means disposed in its entirety within said cylindrical inner wall adjacent the port means, and a space intermediate the closure means and the valve means contained within the inner wall selectively accommodating flow of said liquid therethrough to selectively extend and retract the ram between desired locations.

2. A power unit as defined in claim 1 wherein the valve structure comprises:

a stem supported coaxially within the inner wall for axial movement relative thereto in response to manual actuation to selectively control the fluid communication between said space and said reservoir cavity;

a check valve means comprising a spherical ball and mating seat structure permitting, when the valve structure is open, rapid flow of fluid into said space from the reservoir cavity;

at least one unsealed passage disposed in the mating seat structure of the check valve so as to permit restricted flow of fluid, when the valve structure is open and the check valve is closed between the space and the reservoir cavity.

3. The power unit of claim 1 wherein the U-shaped outer wall comprises an inwardly curved integral end adjacent said pressurized gas so as to efficiently contain the internal pressure of the gas, said outer and inner walls being joined at their respective ends by continuous welds, and wherein the conically converging portion of the outer wall is adjacent said liquid.

4. A power unit for advancing and retracting an object comprising:

hollow ram means comprising means at one end of the hollow ram means adapted to be connected to said object and closure means entirely closing the other end of the ram means, said ram means being relatively reciprocable between extended and retracted positions;

elongated hollow reservoir forming means co-axially and, when in the retracted position, substantially co-extensive with the ram means, the reservoir means comprising a generally elongated annular reservoir cavity defined by a cylindrical inner wall juxtaposed and relatively reciprocable in respect to the ram means, and a generally cylindrical U-shaped outer wall spaced from said inner wall, the respective end of the inner and outer walls being integrally connected to each other, said inner wall comprising port means adjacent one end thereof, the reservoir cavity containing liquid and pressurized gas acting upon and selectively displacing the liquid through the port means;

valve means disposed in its entirety with said cylindrical inner wall adjacent the port means, and a space intermediate the closure means and the valve means contained within the inner wall selectively accommodating flow of said liquid therethrough to selectively extend and retract the ram between desired locations.

* * * * *